(12) United States Patent
Speller

(10) Patent No.: US 11,672,746 B2
(45) Date of Patent: Jun. 13, 2023

(54) HAIR STYLING AND SUNSCREEN COMPOUND

(71) Applicant: John Speller, Farmingdale, NY (US)

(72) Inventor: John Speller, Farmingdale, NY (US)

( * ) Notice: Subject to any disclaimer, the term of this patent is extended or adjusted under 35 U.S.C. 154(b) by 0 days.

(21) Appl. No.: 17/719,898

(22) Filed: Apr. 13, 2022

(65) Prior Publication Data

US 2023/0149277 A1   May 18, 2023

Related U.S. Application Data

(60) Provisional application No. 63/279,296, filed on Nov. 15, 2021.

(51) Int. Cl.
| | |
|---|---|
| *A61K 8/40* | (2006.01) |
| *A61Q 17/04* | (2006.01) |
| *A61Q 5/06* | (2006.01) |
| *A61K 8/35* | (2006.01) |
| *A61K 8/27* | (2006.01) |
| *A61K 8/37* | (2006.01) |
| *A61K 8/29* | (2006.01) |

(52) U.S. Cl.
CPC ............. *A61K 8/40* (2013.01); *A61K 8/27* (2013.01); *A61K 8/29* (2013.01); *A61K 8/355* (2013.01); *A61K 8/37* (2013.01); *A61Q 5/06* (2013.01); *A61Q 17/04* (2013.01)

(58) Field of Classification Search
None
See application file for complete search history.

(56) References Cited

U.S. PATENT DOCUMENTS

2018/0263891 A1 * 9/2018 Patel .................. C08G 65/00

* cited by examiner

*Primary Examiner* — Nannette Holloman
(74) *Attorney, Agent, or Firm* — Brennan, Manna & Diamond, LLC

(57) ABSTRACT

A combination hairstyling and sunscreen composition. The composition is configured to allow a user to style and set hair while providing protection from ultra-violet rays that can damage skin. A hairstyling component allows users to style their hair and a sunscreen component simultaneously protects the scalp from sun damage. The composition may be formulated in a gel, liquid, or spray consistency for application. Thinning hair is easily styled while the scalp is protected from sunburn without leaving an oily residue.

11 Claims, No Drawings

HAIR STYLING AND SUNSCREEN COMPOUND

CROSS-REFERENCE TO RELATED APPLICATION

The present application claims priority to, and the benefit of, U.S. Provisional Application No. 63/279,296, which was filed on Nov. 15, 2021 and is incorporated herein by reference in its entirety.

FIELD OF THE INVENTION

The present invention generally relates to a combination hair styling sun screening product, and more specifically to a dual purpose compound usable as a hair styling product and a sunscreen for the hair and head simultaneously. Accordingly, the present specification makes specific reference thereto. However, it is to be appreciated that aspects of the present invention are also equally amenable to other like applications, devices, and methods of manufacture.

BACKGROUND

Hairstyling products have had a significant impact on the creation of various hairstyles and trends throughout history. Hair gel is a hairstyle product that is used to stiffen hair into a particular hairstyle. The result is similar to, but stronger than, those hair styles using hair spray. Hair gel is typically used in the hairstyling of men, but it is not gender specific. Hair gel can come in tubes, vessels, small bags, or even in a spray form.

Hair wax is a thicker hair styling product containing wax, which helps hold hair in place. Unlike some products such as hair gel which leave the hair hard in texture, hair wax leaves the hair more pliable. Hair mousse is a different hair styling product that is added to hair for extra volume and shine. It is commonly produced as a foam but can also be configured as a spray. Hair mousse adds volume without causing clumps or buildup to the hair style. It is a lighter alternative to hair gel. Mousse is generally applied to the roots of damp hair before blow drying or styling. Hair tonics are liquid hair moisturizers that also help style hair and hold it in place.

Sunscreen, is a photoprotective topical product for the skin that absorbs or reflects some of the sun's ultraviolet (UV) radiation and thus helps protect against sunburn and most importantly prevent skin cancer. Sunscreens may be packaged as lotions, sprays, gels, foams, sticks, powders and other topical products. Sunscreens are a preferred supplement to clothing, particularly sunglasses, sunhats and special sun protective clothing, and other barrier forms of photoprotection.

Men with a full head of hair have natural protection from the sun just from the hair. Bald men or men with very thin hair can easily apply sunscreen to the skin on their head for protection. For those in between with thinning hair there has been no product to provide protection and good grooming at the same time. The only solution is to wear a hat or use a sunscreen product that leaves their hair dirty or oily looking or use nothing and run the risk of serious ailments like skin cancer.

Accordingly, there is a great need for a better way to protect men with thinning hair from sun damage. Similarly, there is a need for a way for a way for men to style thinning hair. There is also a need for a haircare product designed to style hair and function as sunscreen lotion while outdoors.

There is also a need for a solution to physical barriers, such as a hat, to prevent sunburn on the scalp. Further, there is a need for a sunscreen product designed to prevent sunburn without leaving hair oily and unsanitary.

In this manner, the improved hair styling sunscreen composition of the present invention accomplishes all of the forgoing objectives, thereby providing an easy solution for preventing sunburn to the scalp without damaging the user's hair. A primary feature of the present invention is a haircare product designed to simultaneously style hair and function as sunscreen. The present invention benefits men with shorter or thinning hair, ensuring they can still style their hair how they want but remain protected against excessive sunlight exposure. Finally, the improved hair styling sunscreen composition of the present invention can eliminate the need to wear a hat for protection from the sun.

SUMMARY

The following presents a simplified summary in order to provide a basic understanding of some aspects of the disclosed innovation. This summary is not an extensive overview, and it is not intended to identify key/critical elements or to delineate the scope thereof. Its sole purpose is to present some concepts in a simplified form as a prelude to the more detailed description that is presented later.

The subject matter disclosed and claimed herein, in one embodiment thereof, comprises a hair styling sunscreen composition. The hair styling sunscreen composition comprises a styling component and a sunscreen component. The hair styling sunscreen composition is formulated for use as a hair styling product that simultaneously functions as a sunscreen for the scalp. The hair styling sunscreen composition may be formulated in the form of a gel, a liquid, or an aerosol.

The styling component comprises at least one conditioning agent. The at least one conditioning agent may be an anti-static agent, a cationic surfactant, a humectant or moisturizer, an emollient or oil, an occlusive agent, a protein conditioning agent, a silicone, or a polymer. The styling component may further comprise at least one thickening agent. The at least one thickening agent may be carbomer, an acrylate copolymer, any similar free-flowing polymer, or the like. The styling component may further comprise at least one fixative agent. The at least one fixative agent may be a styling polymer, such as polyvinyl pyrolidone or vinyl pyrolidone, benzyl benzoate, natural thickeners, or the like.

The sunscreen component comprises at least one organic ultraviolet absorbing ingredient, at least one formulation stabilizing ingredient, and at least one sensory enhancer ingredient. The at least one organic ultraviolet absorbing ingredient may be a plurality of organic ultraviolet absorbing ingredients. The plurality of organic ultraviolet absorbing ingredients are the "active" ingredients in the sunscreen component and act as a chemical sunscreen. The plurality of organic ultraviolet absorbing ingredients are present in the sunscreen component in a range of between 20-30% by weight. The plurality of organic ultraviolet absorbing ingredients may be avobenzone, homosalate, octisalate, octocrylene, or any combination thereof.

The at least one formulation stabilizing ingredient may be a plurality of formulation stabilizing ingredients. A quantity of the plurality of formulation stabilizing ingredients are present in the sunscreen component in a range of between 50-60% by weight. The plurality of formulation stabilizing ingredients may comprise a solvent, a thickening agent, an emulsifier, a chelating agent, or any combination thereof.

The at least one sensory enhancer ingredient may be a plurality of sensory enhancer ingredients. A quantity of the plurality of sensory enhancer ingredients are present in the sunscreen component in a range of between 10-20% by weight. The plurality of sensory enhancer ingredients may comprise a moisturizer, a fragrance, an emollient, or any combination thereof.

To the accomplishment of the foregoing and related ends, certain illustrative aspects of the disclosed innovation are described herein in connection with the following description and the annexed drawings. These aspects are indicative, however, of but a few of the various ways in which the principles disclosed herein can be employed and is intended to include all such aspects and their equivalents. Other advantages and novel features will become apparent from the following detailed description when considered in conjunction with the drawings.

DETAILED DESCRIPTION

The innovation is now described with reference to the drawings, wherein like reference numerals are used to refer to like elements throughout. In the following description, for purposes of explanation, numerous specific details are set forth in order to provide a thorough understanding thereof. It may be evident, however, that the innovation can be practiced without these specific details. In other instances, well-known structures and devices are shown in block diagram form in order to facilitate a description thereof. Various embodiments are discussed hereinafter. It should be noted that the figures are described only to facilitate the description of the embodiments. They do not intend as an exhaustive description of the invention or do not limit the scope of the invention. Additionally, an illustrated embodiment need not have all the aspects or advantages shown. Thus, in other embodiments, any of the features described herein from different embodiments may be combined.

The present invention is an improved hair styling sunscreen composition formulated to prevent sunburn to the scalp without damaging the user's hair. A primary feature of the present invention is a haircare product designed to simultaneously style hair and function as sunscreen. The present invention benefits men with shorter or thinning hair, ensuring they can still style their hair how they want but remain protected against excessive sunlight exposure. Finally, the improved hair styling sunscreen composition of the present invention is capable of eliminating the need to wear a hat for protection from the sun.

The hair product features a styling gel-like component and integrated suntan lotion. In one embodiment the product may be comprised of, but not limited to, denatured alcohol, ppg-40 butyl ether (polypropylene glycol ether of butyl alcohol), water, benzyl benzoate, fragrance, dihydroabietyl alcohol, d&c yellow no. 10, fd&c yellow no. 6, avobenzone, homosalate, octisalate, octocrylene, aluminum starch octenylsuccinate, styrene/acrylates copolymer, glycerin, polyester-27, silica, phenoxyethanol, isododecane, arachidyl alcohol, beeswax, ethylhexylglycerin, neopentyl glycol diheptanoate, acrylates/c10-30 alkyl acrylate cross polymer, behenyl alcohol, tocopherol (vitamin e), arachidyl glucoside, glyceryl stearate, peg-100 stearate, potassium hydroxide, disodium edta, and sodium ascorbyl phosphate.

The combination product can help control hair and leave it manageable, allowing users to style hair how they wish. When the individual spends time outdoors, they are protected against harmful UV rays, effectively preventing sunburn and potential ailments like skin cancer. The hair product may be formulated in the form of a gel, a liquid, or an aerosol.

The present invention, in one exemplary embodiment, is a hair styling sunscreen composition. The hair styling sunscreen composition comprises a styling component and a sunscreen component. The hair styling sunscreen composition is formulated for use as a hair styling product, such as a gel, a tonic, a mousse, a wax, or the like, that simultaneously functions as a sunscreen for the scalp. The hair styling sunscreen composition may be formulated in the form of a gel, a liquid, or an aerosol. The hair styling sunscreen composition may be rubbed or sprayed onto the scalp.

The styling component is formulated for use as a hair styling product. The styling component comprises at least one conditioning agent. The at least one conditioning agent may be an anti-static agent, a cationic surfactant, a humectant or moisturizer, an emollient or oil, an occlusive agent, a protein conditioning agent, a silicone, a polymer, or any combination thereof. The at least one conditioning agent can produce a film on skin or hair, attract and bind water, lubricate, or provide other conditioning properties to hair. The at least one conditioning agent may also be a tonic oil.

The styling component may further comprise at least one thickening agent. The at least one thickening agent may be carbomer, an acrylate copolymer, any similar free-flowing polymer, or the like designed to add volume or the appearance of volume. The styling component may further comprise at least one fixative agent. The at least one fixative agent may be a styling polymer, such as polyvinyl pyrolidone or vinyl pyrolidone, benzyl benzoate, natural thickeners, or the like. The at least one fixative agent is formulated to hold hair in place once styled.

The sunscreen component comprises at least one organic ultraviolet absorbing ingredient, at least one formulation stabilizing ingredient, and at least one sensory enhancer ingredient. The sunscreen component is formulated to protect skin from UV-A and UV-B light. UV-A light has longer wavelengths compared to UVB rays and are approximately 90% more common at the earth's surface. UV-B light can damage the DNA in the epidermis, as well as cause sunburn. UV-A rays can penetrate to the dermis causing minor damage, such as tanning and wrinkles, as well as triggering DNA damage that can lead to skin cancer.

UV filters fall into one of two categories: mineral (or physical) or organic (or chemical) sunscreens. The at least one organic ultraviolet absorbing ingredient is the organic or chemical sunscreen category. Organic or chemical sunscreens work by absorbing and dissipating the energy of the photons. The at least one organic ultraviolet absorbing ingredient may be a plurality of organic ultraviolet absorbing ingredients. The plurality of organic ultraviolet absorbing ingredients are the "active" ingredients in the sunscreen component that filter the sun and act as a chemical sunscreen.

A quantity of the plurality of organic ultraviolet absorbing ingredients are typically present in the sunscreen component in a range of between approximately 20-30% by weight but may be more or less as desired. The plurality of organic ultraviolet absorbing ingredients may be avobenzone, homosalate, octisalate, octocrylene, or any combination thereof. These ingredients are desirable as they each have a benzene ring to absorb the photon and then dispense that light energy as heat energy.

The at least one formulation stabilizing ingredient may be a plurality of formulation stabilizing ingredients. A quantity of the plurality of formulation stabilizing ingredients are present in the sunscreen component in a range of between approximately 50-60% by weight but may be more or less as desired. The plurality of formulation stabilizing ingredients may comprise a solvent, a thickening agent, an emulsifier, a chelating agent, or any combination thereof. These ingredients are advantageous as they generally help keep the active ingredients in solution, homogeneous, spreadable, and functional. The largest proportion of these ingredients are the solvents, which is usually water, and oils.

The at least one sensory enhancer ingredient may be a plurality of sensory enhancer ingredients. A quantity of the plurality of sensory enhancer ingredients are present in the sunscreen component in a range of between approximately 10-20% by weight but may be more or less as desired. The plurality of sensory enhancer ingredients may comprise a moisturizer, a fragrance, an emollient, or any combination thereof. Sensory enhancers are advantageous as they change the way the compound feels or smells.

The sunscreen component may further comprise at least one mineral ultraviolet filter ingredient. The at least one mineral ultraviolet filter create a physical barrier on the skin and may be titanium dioxide or zinc oxide. The sunscreen component may further comprise a humectant. The humectant, such as glycerin or aloe, is beneficial to attract moisture. The sunscreen component may further comprise a blue light blocking ingredient. The blue light blocking ingredient is beneficial to deter blue light oxidation on skin. The sunscreen component may further comprise an antioxidant ingredient. The antioxidant ingredient is useful to absorb the free radicals generated by the active ingredients.

The following ingredients are being submitted to further define various species of the present disclosure. These examples are intended to be illustrative only and are not intended to limit the scope of the present disclosure. Also, parts and percentages are by equivalent volume units, unless otherwise indicated. Tables 1-3 provide the ingredients by type.

TABLE 1

| Styling Component Ingredients | Function |
| --- | --- |
| Denatured Alcohol | Solvent |
| PPG-40 Butyl Ether | Conditioning Agent |
| Benzyl Benzoate | Fixative |
| Fragrance | Fragrance |
| Dihydroabietyl alcohol | Plasticizer |
| D&C Yellow No. 10 | Colorant |
| FD&C Yellow No. 6 | Colorant |
| Water | Solvent |

This list of ingredients represents one embodiment of a typical formulation of the styling component.

TABLE 2

| Sunscreen Component Active Ingredients | percentage by wt. |
| --- | --- |
| avobenzone | 3% |
| homosalate | 10% |
| octisalate | 4.50% |
| octocrylene | 8% |

This list of ingredients represents one embodiment of a typical formulation for the plurality of organic ultraviolet absorbing ingredients of the sunscreen component.

TABLE 3

| Sunscreen Component Inactive Ingredients |
| --- |
| Water |
| Aluminum Starch Octenylsuccinate |
| Styrene/Acrylates Copolymer |
| Glycerin |
| Polyester-27 |
| Silica |
| Phenoxyethanol |
| Isododecane |
| Arachidyl Alcohol |
| Beeswax |
| Ethylhexylglycerin |
| Neopentyl Glycol Diheptanoate |
| Acrylates/C10-30 Alkyl Acrylate Crosspolymer |
| Behenyl Alcohol |
| Tocopherol (Vitamin E) |
| Arachidyl Glucoside |
| Glyceryl Stearate |
| PEG-100 Stearate |
| Potassium Hydroxide |
| Disodium EDTA |
| Sodium Ascorbyl Phosphate |
| Fragrance |

This list of ingredients represents one embodiment of a typical formulation for the plurality of formulation stabilizing ingredients and the plurality of sensory enhancing ingredients of the sunscreen component.

Notwithstanding the forgoing, the hair styling sunscreen composition can be any suitable composition or configuration as is known in the art without affecting the overall concept of the invention, provided that it accomplishes the above stated objectives. One of ordinary skill in the art will appreciate that the ingredients and percentages the hair styling sunscreen composition, as show in the Tables are for illustrative purposes only, and that many other ingredients and percentages of the hair styling sunscreen composition are well within the scope of the present disclosure. As such, the hair styling sunscreen composition may be comprised of ingredients and percentages that is appropriate and specific in regard to whatever the hair styling sunscreen composition is designed to be applied.

What has been described above includes examples of the claimed subject matter. It is, of course, not possible to describe every conceivable combination of components or methodologies for purposes of describing the claimed subject matter, but one of ordinary skill in the art may recognize that many further combinations and permutations of the claimed subject matter are possible. Accordingly, the claimed subject matter is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:
1. A hair styling sunscreen composition comprising:
a styling component comprising a mixture of denatured alcohol, PPG-40 butyl ether, benzyl benzoate, a fragrance; dihydroabietyl alcohol, D&C yellow number 10 colorant, FD&C yellow number 6 colorant, and water formulated as a gel, a liquid, or an aerosol; and a sunscreen component comprising:
  a plurality of organic ultraviolet absorbing ingredients, and wherein a quantity of the of the plurality of organic ultraviolet absorbing ingredients are present in the sunscreen component in a range of between 20-30% by weight;
  a plurality of formulation stabilizing ingredients, and wherein a quantity of the plurality of formulation stabilizing ingredients are present in the sunscreen component in a range of between 50-60% by weight, wherein one of the plurality of formulation stabilizing ingredients is a chelating agent; and
  a plurality of sensory enhancer ingredients, and wherein a quantity of the plurality of sensory enhancers are present in the sunscreen component in a range of between 10-20% by weight.

2. The hair styling sunscreen composition of claim 1, wherein the sunscreen component further comprises a humectant.

3. The hair styling sunscreen composition of claim 1, wherein the sunscreen component further comprises a blue light blocking ingredient.

4. The hair styling sunscreen composition of claim 1, wherein the sunscreen component further comprises at least one mineral ultraviolet filter ingredient.

5. The hair styling sunscreen composition of claim 4, wherein the at least one mineral ultraviolet filter ingredient is titanium dioxide or zinc oxide.

6. The hair styling sunscreen composition of claim 1, wherein the sunscreen component further comprises at least one antioxidant ingredient.

7. The hair styling sunscreen composition of claim 1, wherein the plurality of organic ultraviolet absorbing ingredients are a combination of avobenzone, homosalate, octisalate, and octocrylene.

8. The hair styling sunscreen composition of claim 1, wherein the plurality of formulation stabilizing ingredients further comprise a solvent, a thickening agent, and an emulsifier.

9. The hair styling sunscreen composition of claim 1, wherein the plurality of sensory enhance ingredients comprise a moisturizer, a fragrance, and an emollient.

10. The hair styling sunscreen composition of claim 1, wherein the hair styling sunscreen composition is in the form of a gel or a liquid.

11. A hair styling sunscreen composition comprising:
a styling component comprising:
  at least one thickening agent;
  at least one fixative ingredient; and
  at least one conditioning agent; and
a sunscreen component comprising:
  a plurality of organic ultraviolet absorbing ingredients comprising avobenzone, homosalate, octisalate, and octocrylene, and wherein a quantity of the avobenzone is present in the sunscreen component at about 3% by weight, a quantity of the homosalate is present in the sunscreen component at about 10% by weight, a quantity of the octisalate is present in the sunscreen component at about 4.5% by weight, and a quantity of the octocrylene is present in the sunscreen component at about 8% by weight; and
  a plurality of formulation stabilizing ingredients, and wherein a quantity of the plurality of formulation stabilizing ingredients are present in the sunscreen component in a range of between 50-60% by weight, wherein one of the plurality of formulation stabilizing ingredients is a chelating agent; and
  a plurality of sensory enhancer ingredients, and wherein a quantity of the plurality of sensory enhancers are present in the sunscreen component in a range of between 10-20% by weight; and
  wherein the plurality of formulation stabilizing ingredients and the plurality of sensory enhancer ingredients comprise a mixture of water, Aluminum Starch Octenylsuccinate, Styrene/Acrylates Copolymer, Glycerin, Polyester-27, Silica, Phenoxyethanol, Isododecane, Arachidyl Alcohol, Beeswax, Ethylhexylglycerin, Neopentyl Glycol Diheptanoate, Acrylates/C10-30 Alkyl Acrylate Crosspolymer, Behenyl Alcohol, Tocopherol, Arachidyl Glucoside, Glyceryl Stearate, PEG-100 Stearate, Potassium Hydroxide, Disodium EDTA, Sodium Ascorbyl Phosphate, and at least one fragrance.

* * * * *